United States Patent [19]

Ams et al.

[11] Patent Number: 5,047,010
[45] Date of Patent: Sep. 10, 1991

[54] EQUIPMENT FOR THE CONTROLLED INSUFFLATION OF A FLUID INTO A BODY CAVITY

[75] Inventors: Felix Ams, Kämpfelbach; Manfred Baier, Bretten, both of Fed. Rep. of Germany

[73] Assignee: Richard Wolf GmbH, Knittlingen, Fed. Rep. of Germany

[21] Appl. No.: 493,522

[22] Filed: Mar. 14, 1990

[30] Foreign Application Priority Data

Apr. 17, 1989 [DE] Fed. Rep. of Germany ....... 3912541

[51] Int. Cl.$^5$ ............................................. A61M 37/00
[52] U.S. Cl. ...................................... 604/26; 128/747; 128/748
[58] Field of Search ............... 128/747, 748, DIG. 12, 128/DIG. 13; 604/23, 26, 27, 28, 31

[56] References Cited

U.S. PATENT DOCUMENTS

| | | | |
|---|---|---|---|
| 3,858,572 | 1/1975 | Binard et al. | 604/26 |
| 4,464,169 | 8/1984 | Semm | 604/26 |
| 4,538,594 | 9/1985 | Boebel et al. | 128/6 |
| 4,676,774 | 6/1987 | Semm et al. | 604/26 |
| 4,735,603 | 4/1988 | Goodson et al. | 128/747 |
| 4,874,362 | 10/1989 | Wiest et al. | 128/747 |
| 4,966,578 | 10/1990 | Baier et al. | 604/26 |

FOREIGN PATENT DOCUMENTS 3000218 6/1983 Fed. Rep. of Germany.
3329784 10/1987 Fed. Rep. of Germany.

Primary Examiner—Stephen C. Pellegrino
Assistant Examiner—Michael Rafa
Attorney, Agent, or Firm—Panitch Schwarze Jacobs & Nadel

[57] ABSTRACT

Equipment is disclosed for the controlled insufflation of a fluid into a body cavity through a probe inserted thereinto, particularly for insufflating gas through the conduit of an endoscope partly inserted into the body cavity. The equipment comprises a supply device for delivering the fluid and on which a selected nominal value for the pressure in the body cavity can be set and the relevant actual value of the body cavity pressure can be displayed by means of a measuring instrument. The inlet side of a circulating pump, is connected by way of a filter to the body cavity. During an operation the pump draws off fluid from the body cavity and circulates it back to the body cavity. Part of the circuit on the delivery side of the pump and part of the circuit leading to the measuring instrument have a common portion leading to the body cavity. When the pump is running, therefore, a retroactive dynamic pressure is applied to the measuring instrument. The dynamic pressure is compensated for by a partial vacuum derived from the delivery flow of the pump.

7 Claims, 1 Drawing Sheet

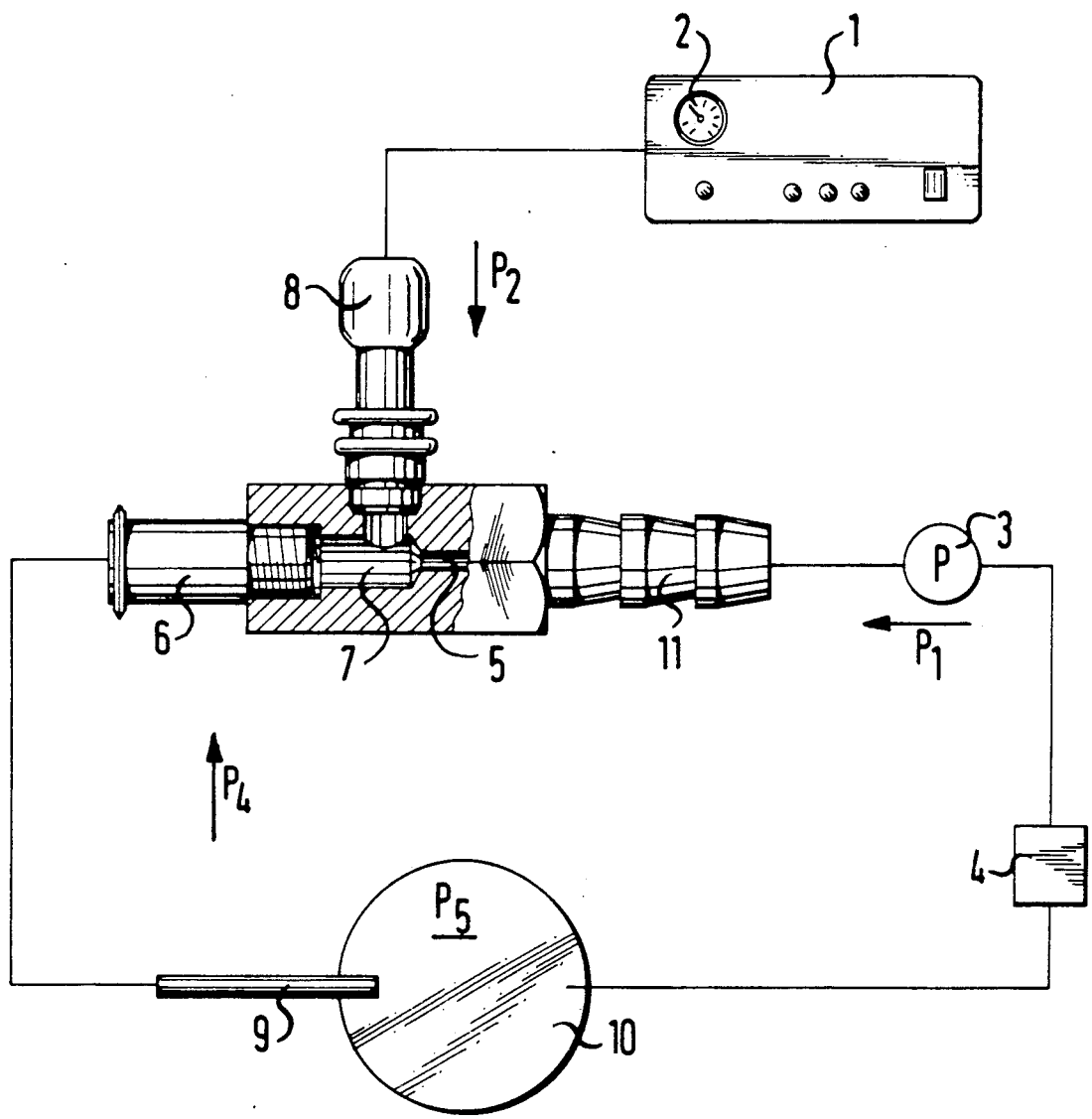

5,047,010

EQUIPMENT FOR THE CONTROLLED INSUFFLATION OF A FLUID INTO A BODY CAVITY

FIELD OF THE INVENTION

This invention relates to equipment for the controlled insufflation of a fluid into a body cavity. When carrying out an endoscopic operation in an animal or in a human body cavity the integuments, for example the abdominal wall, must often be lifted clear of the internal organs in the cavity by insufflating a suitable gas, for example $CO_2$, in order to provide free space for instruments to be inserted into said cavity.

BACKGROUND OF THE INVENTION

For achieving the most constant possible pressure in the body cavity during the operation, there may be used an insufflation device such as that disclosed in DE-B-30 00 218, for example. In this case the gas is supplied to the body cavity from a gas container by way of an intermediate container, a pressure reducer, a stop valve, a pressure measuring instrument and a flow display device and by way of an admission pipeline and a cannula penetrating the integument.

Where a coagulation instrument is passed through the endoscope, for coagulating tissue, blood vessels and the like, its use causes smoke and steam to be produced in the body cavity, obscuring the operator's view of the operation. In order to avoid this disadvantage, a smoke filter circuit, as described in DE-B-33 29 784, for example, may be employed. This consists of a pump, a conduit and a filter. Insufflation gas mixed with smoke and steam is drawn off from the body cavity by the pump, is led through the conduit to the smoke filter, is cleaned in the filter and is finally returned to the body cavity.

In an insufflation procedure it is now usual for a nominal pressure for the body cavity to be set on an insufflation gas supply device and the body cavity to be filled with the insufflation gas until said nominal value has been reached, so as to keep the body cavity pressure as constant as possible during the operation. The constancy of said pressure, may, however, be disturbed by loss of gas caused, for example, by resorption of gas into the body, or by gas leaking at the entry point of the cannula into the body cavity. The resulting loss of pressure in the body cavity must be compensated for during the operation, by producing a regular slight inflow of gas into said cavity. The reference value for regulating such inflow is the nominal value which was set initially. The inflow must be controlled to achieve said nominal value, and to do this, the actual value of the pressure in the body cavity must be measured. Such measurement is generally effected at the pipe by means of which the gas is introduced into the body cavity, in order to avoid the need for making a second puncture therein.

The instruments and pipes normally used in endoscopy, are of such small cross section, that a difference in pressure occurs which distorts the measurement of said actual pressure so that the compensating gas inflow is difficult to control.

Such distortion is increased where a waste gas filter circuit is in operation for cleaning the insufflation gas as described above, since the output of the pump of the waste gas filter circuit is considerably higher than the output of the insufflation gas supply device when operated to deliver small amounts of gas in order to compensate for gas losses.

If the pipe of the waste gas filter circuit is connected to a pipe common to it, and to the gas supply device, in order to avoid the need for providing a further entry point in the body cavity, the said pump will, when in operation, generate such high dynamic pressure in the common pipe that, the measurement of the actual value of the pressure in the body cavity will be falsified so that the actual value will generally appear to be much greater that it really is.

It has been found that the said dynamic pressure may be many times greater than the desired pressure in the body cavity.

Such falsification of the measurement of said actual value prevents adjustment of the pressure in the body cavity until the sum of the actual value of the body cavity pressure and the said dynamic pressure falls below the nominal value of the pressure in the body cavity, whereby the body cavity may be completely emptied when gas has been lost, without adjustment of the pressure therein.

SUMMARY OF THE INVENTION

An object of the present invention is in equipment of the kind described above, to make it possible to remove waste gas from the body cavity as needed during the operation, the real or actual value of the pressure in the intra-abdominal body cavity being measured and displayed, while the nominal value of the pressure in the body cavity is maintained through the waste gas outlet without disadvantage.

An equipment according to the invention comprises a supply device for delivering the insufflation fluid to the body cavity by means of a probe, and on which the relevant nominal value for the pressure in the body cavity can be set and the relevant actual value of the body cavity pressure can be displayed by means of a measuring instrument. The inlet side of a waste gas filter circulation pump is connected by way of a filter to the body cavity. The pump draws off fluid from the body cavity and circulates the filtered fluid back to the body cavity. Part of the circuit on the delivery side of the pump and part of the circuit leading to the measuring instrument follow a common path to the body cavity, in which path when the pump is running there is a retroactive dynamic pressure on the measuring instrument. So that said dynamic pressure can be compensated for by a partial vacuum derived from the delivery flow of the pump and being retroactive on the measuring instrument, the said dynamic pressure and the said partial vacuum are of the same value, independently of the relevant delivery flow.

Said partial vacuum may be produced by a fluid entrainment pump, having a longitudinal conduit, fitted with a nozzle, through which the pumping medium of the circulation pump flows. A suction connection ending in the longitudinal conduit, which is of enlarged cross section, at that point, behind the nozzle, in the direction of flow, is connected to the measuring instrument.

The fluid entrainment pump is preferably in the form of a T-piece having three branches, the nozzle being arranged in the first branch which is connected to the waste gas filter circulation pump, the second branch, which lies on the same axis as the first branch, being connected to the probe which may be that of an endoscope and the third branch being connected to the measuring instrument.

Said common path of the pump circuit and the circuit leading to the measuring instrument may begin at the second branch of the T-piece.

The effective cross-section of the nozzle and thus the value of the partial vacuum for compensating for the said dynamic pressure, can be exactly adapted to the dynamic pressure which is anticipated in each case.

The effective cross section of the nozzle may be arranged to be adjustable in order to adjust the value of the partial vacuum. To this end an adjustable diaphragm may be disposed in the nozzle, which can be closed or opened to adapt the effective cross section of the nozzle to the required value of the dynamic pressure that is anticipated.

BRIEF DESCRIPTION OF THE DRAWING

The drawing is a diagram of one embodiment of equipment according to the invention, for the controlled insufflation of a fluid into a body cavity.

DETAILED DESCRIPTION OF THE INVENTION

The equipment comprises a fluid supply device 1 for delivering insufflation fluid into a body cavity 10 by way of an insufflation circuit comprising conduits, through a probe 9 of an endoscope, inserted into the body cavity 10. The supply device 1 comprises a measuring instrument 2 which continuously displays the real or actual value of the fluid pressure in the body cavity 10, and means for setting a nominal value for such pressure.

A waste gas filter circuit comprises conduits, a circulating pump 3 and a waste gas filter 4, for drawing off gas mixed with steam from the body cavity 10, filtering it, and returning into the body cavity 10 through the probe 9 of the endoscope.

The insufflation circuit and the waste gas filter circuit are so coupled together that part of the delivery side of the waste gas filter circuit and part of insufflation circuit are common to both circuits.

The circuits are coupled by means of a fluid entrainment pump in the form of a T-piece having three branches 6, 8 and 11, the branch 11 being connected to the pump 3, the leg 8 being connected to the supply device 1 and the branch 6 being connected to the probe 9 of the endoscope. The branch 11 lies on the same axis as the branch 6. Fluid flowing into the entrainment pump through the branch 11 reaches a larger cross section longitudinal conduit 7 through a nozzle 5, into which conduit 7 fluid from the supply device 1 discharges through the branch 8. The fluid reaches the probe 9 of the endoscope from the conduit 7 by way of the branch 6.

During initial insufflation, that is to say, at the beginning of an endoscopic operation, fluid is conducted from the supply device 1 through the branch 8, the conduit 7 and the branch 6, to the probe 9 until the nominal value for the fluid pressure in the body cavity, which value has been set by said setting means of the supply device 1 has been reached.

It may now be expected that there will be a loss of gas in, or near to, the body cavity 10, which should be compensated for by the supply of a small amount of gas from the supply device 1. For regulating such supply of gas the actual value of the pressure in the body cavity 10 must be recorded, and this is usually carried out through the same conduit.

If the waste gas filter circuit must now be put into operation, for example because the gas in the body cavity 10 is mixed with steam as a result of coagulation, the pump 3 is started. The output of the pump 3 of the waste gas filter circuit will, however, be many times greater than the output of the supply device 1 when compensating for the loss of gas.

A correspondingly greater dynamic pressure $P_4$ is built up in the conduit between the branch 6 of the fluid entrainment pump and the probe 9 of the endoscope. If no compensation for the loss of gas were carried out, the measuring instrument 2 of the supply device 1 would display an actual value for the pressure in the body cavity 10, consisting of the sum of the real or actual body cavity pressure $P_5$ and the dynamic pressure $P_4$. The sum of these pressures $P_4$ and $P_5$ would also be input into the pressure control means of the supply device 1, so that the pressure in the body cavity 10 would not be controllable on the basis of the said nominal value which had been set.

The fluid entrainment pump is, however, arranged to remedy this disadvantage.

A partial vacuum $P_3$, of the same value as the dynamic pressure $P_4$, is produced to the branch 8 by virtue of the relatively high delivery rate of the pump 3. The measured value of the pressure applied to the supply device 1 is, therefore, continuously equal to the real pressure $P_5$ in the body cavity 10, as will appear from the following equations, in which $P_1$ is the pressure produced in the pump 3:

$$P_1 + P_2 - P_3 = 0$$

$$P_1 - P_4 + P_5 = 0$$

from which it follows that:

$$P_2 + P_4 - P_5 - P_3 = 0$$

using the assumption:

$$|P_3| = |P_4|$$

it follows that:

$$P_2 = P_5.$$

On the basis of the above ratios the pressure in the body cavity 10 can be post-regulated to equal the said preset nominal value, even whilst the pump 3 is operating.

The effective cross section of the nozzle 5 and thus the partial vacuum $P_3$ compensating for the dynamic pressure $P_4$ can be exactly adapted to the dynamic pressure $P_4$ which can be anticipated in each case, insofar as the pressure ratios are a priori stable.

The effective cross section of the nozzle 5 may be variable, so that pressure compensation accorded thereby can be adapted to unknown or changing pressure ratios.

What is claimed is:

1. Equipment for the controlled insufflation of a fluid into a body cavity by way of a probe inserted thereinto; the equipment comprising:
    a supply device for delivering said fluid to said probe and being connected to said probe by means of a first fluid circuit the supply device having means for setting a nominal fluid pressure value for the body cavity and means for measuring and indicating the actual value of the fluid pressure in the body cavity;

a circulating pump having an inlet side connected to a filter for connection to the body cavity, for drawing off fluid therefrom by way of the filter and a delivery side connected to the probe by way of a second fluid circuit for returning filtered fluid to the body cavity, said first and second fluid circuits having a common portion extending to said probe and in which, when the pump is in operation, there is generated retroactive dynamic pressure acting upon said measuring means; and means for deriving from the delivery flow of the circulating pump a partial vacuum for acting retroactively upon said measuring means and being of a value to compensate for said dynamic pressure independently of the delivery flow of the circulating pump.

2. Equipment as claimed in claim 1, wherein said deriving means comprises a fluid entrainment pump having a longitudinal conduit, a nozzle communicating therewith and being connected to the delivery side of the circulating pump, and a suction connection debouching into the longitudinal conduit proximate to said nozzle which is of smaller cross sectional area than the longitudinal conduit, said suction connection being connected to said measuring means.

3. Equipment as claimed in claim 2, wherein the fluid entrainment pump is in the form of a T-shaped element having first, second and third branches, the nozzle being disposed in the first branch, the second branch being axially aligned with the first branch and being connected to the probe and the third branch being connected to the measuring means.

4. Equipment as claimed in claim 3, wherein said common portion of said first and second fluid circuits extends from said second branch to said probe.

5. Equipment as claimed in claim 2, wherein said nozzle has an effective cross section which is selected so as precisely to adapt the value of said partial vacuum to compensate for said dynamic pressure.

6. Equipment as claimed in claim 2, further comprising means for adjusting the effective cross section of said nozzle for precisely adapting the value of said partial vacuum to compensate for said dynamic pressure.

7. Equipment as claimed in claim 1, wherein said probe is an endoscope for partial insertion into the body cavity and having a conduit for insufflating gas therethrough and into the body cavity.

* * * * *